(12) United States Patent
Chen et al.

(10) Patent No.: US 9,937,110 B2
(45) Date of Patent: Apr. 10, 2018

(54) TRANSLUCENT GEL SYSTEM

(71) Applicant: RHODIA OPERATIONS, Paris (FR)

(72) Inventors: Xi Chen, Singapore (SG); Hai Zhou Zhang, Singapore (SG)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/787,511

(22) PCT Filed: Apr. 23, 2014

(86) PCT No.: PCT/EP2014/058225
§ 371 (c)(1),
(2) Date: Oct. 28, 2015

(87) PCT Pub. No.: WO2014/177438
PCT Pub. Date: Nov. 6, 2014

(65) Prior Publication Data
US 2016/0067153 A1    Mar. 10, 2016

(30) Foreign Application Priority Data

Apr. 30, 2013  (WO) ................. PCT/EP2013/058992

(51) Int. Cl.
*A61K 8/04* (2006.01)
*A61K 8/36* (2006.01)
*A61K 8/45* (2006.01)
*A61K 8/41* (2006.01)
*A61Q 5/12* (2006.01)

(52) U.S. Cl.
CPC .............. *A61K 8/042* (2013.01); *A61K 8/361* (2013.01); *A61K 8/416* (2013.01); *A61K 8/45* (2013.01); *A61Q 5/12* (2013.01); *A61K 2800/262* (2013.01)

(58) Field of Classification Search
None
See application file for complete search history.

(56) References Cited

U.S. PATENT DOCUMENTS 6,315,991 B1 * 11/2001 Zofchak .................. A61K 8/87
424/70.28

FOREIGN PATENT DOCUMENTS

EP         2216011 A2    8/2010
WO    2008/145579 A2   12/2008

* cited by examiner

Primary Examiner — Aradhana Sasan

(57) ABSTRACT

The present invention concerns a translucent gel system, notably a hair conditioner gel, comprising at least a carboxylic acid, an alkoxylated alkyl or alkenyl amine and a cationic surfactant. Such a translucent gel system provides an excellent conditioning effect for washing skin and/or hair and a high transmittance.

21 Claims, No Drawings

TRANSLUCENT GEL SYSTEM

This application is a U.S. national stage entry under 35 U.S.C. § 371 of International Patent Application No. PCT/EP2014/058225, filed Apr. 23, 2014, which claims priority to EP Patent Application No. PCT/EP2013/058992, filed on Apr. 30, 2013, the whole content of each of these applications is hereby incorporated herein by reference for all purposes.

The present invention concerns a translucent gel system, notably a hair conditioner gel, comprising at least a carboxylic acid, an alkoxylated alkyl or alkenyl amine and a cationic surfactant. Such a translucent gel system provides an excellent conditioning effect for washing skin and/or hair and a high transmittance.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Human hair requires cleaning, since the hair fibers become soiled, both from environmental contamination as well as contamination and soiling from chemical agents produced by the body. Generally, shampooing is employed to clean the hair by removing excess soil and body oils which have built up on the hair fibers. Unfortunately, while being capable of cleaning the hair fibers, shampoos generally leave the hair stripped, over-processed and difficult to manage. Recently, gel formulations of hair conditioners have become popular. There are extensive researches to develop new hair conditioner gels matching with the need of the market and the different users, notably relative to the hair conditioning effects but also on the formulations aspects such as viscosity or colours and shades.

For particular market segments, there is a need to obtain translucent gel system. Several hair conditioner gels may be found on the market but all of them are not translucent due to the presence of fatty alcohol or silicone, such as cetyl alcohol, stearyl alcohol or dimethicone, within the formulations. Other products are known for their translucent ability but can not be used as they show a negative impact on the gel obtaining leading to either a drastic drop of viscosity or compatibility issue, such as polymerized short chain carboxylic acids.

Thus, there is a need for a translucent gel system, notably for hair conditioner, providing a gel with a sufficient viscosity, an excellent conditioning effect for hair and a high transmittance.

INVENTION

The above-listed needs are met or exceeded by the present invention focused on a translucent gel system, notably a hair conditioner gel, comprising at least a carboxylic acid, an alkoxylated alkyl or alkenyl amine and a cationic surfactant. Such a translucent gel system provides an excellent conditioning effect for washing skin and/or hair and a high transmittance.

The formulation of the present invention also provides a gel-type hair conditioner having the characteristic features described above which is capable of being applied directly to the head of hair quickly and easily by merely spraying the gel formulation on the hair or via a container that is pumped through an orifice. The formulation of the invention also permits to obtain a greater control over the placement and the amount of hair conditioner applied to the hair. Still another need is for a hair styling device which reduces the time required in the hair styling process. In addition, the present translucent gel system and its ability to be spread out on the hair without shading the hair reduces the time required for hair styling.

Gel systems of the present invention also provide a good time and temperature stability notably after storage at high and low temperature. A consistent and uniform appearance is important for a product as in the real situation, a product in the market or kept by consumer would be stored in cold or hot temperature and a big change on the appearance over different temperatures or over a period of time within shelf life will not be accepted by consumers.

The present invention then concerns a gel system, notably a translucent gel system, comprising at least:
(1) 1-10% by weight of a carboxylic acid having an alkyl or alkenyl chain comprising from 8 to 22 carbon atoms;
(2) 1-10% by weight of an alkoxylated alkyl or alkenyl amine;
(3) 0.5-5% by weight of a cationic surfactant; and
(4) water.

The present invention also concerns a gel system, notably a translucent gel system, susceptible to be obtained by mixing at least the above identified components.

These compositions of the invention may be formulated for washing skin and/or hair, for example, bath or shower gels, handwashing compositions, facial washing compositions, pre- and post-shaving products, and rinse-off and wipe-off skin care products, and mainly to produce cleansing foam, body shampoo and hair shampoo.

Other characteristics, details and advantages of the invention will emerge even more fully upon reading the description which follows.

Throughout the description, including the claims, the term "comprising one" should be understood as being synonymous with the term "comprising at least one", unless otherwise specified, and "between" should be understood as being inclusive of the limits.

"Alkyl" as used herein means a straight chain or branched saturated aliphatic hydrocarbon. As used herein, unless stated otherwise, the term "alkyl" means a linear or branched alkyl group optionally substituted with one or more substituent selected from the group consisting of alkyl, alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Alkenyl", as used herein, refers to a straight chain or branched aliphatic group containing at least one double bond and is intended to include both "unsubstituted alkenyls" and "substituted alkenyls", the latter of which refers to alkenyl moieties having substituents replacing a hydrogen on one or more carbon atoms of the alkenyl group.

As used herein, the term "alkoxylated" means that the compound comprises one or more alkoxy or, more typically, poly(alkyleneoxy) moieties, such as, for example a poly (ethyleneoxy), poly(propyleneoxy), or poly(ethlyeneoxypropyleneoxy) moiety and the term "ethoxylated" means that the compound comprises at least one ethoxy or poly (ethyleneoxy) moiety.

Preferably the gel system provides an apparent viscosity comprised between 1000 and 100000 cps, more preferable comprised between 3000 and 50000 cps, notably between 3000 and 35000 cps, particularly between 3000 and 25000 cps. The apparent viscosity is preferably measured on a Brookfield DV-II+ viscometer at 25° C., 10 rpm for 1 minute.

Preferably the gel system provides a transmittance comprised between 1 and 100%, more preferably between 3 and 100%, more preferably comprised between 5 and 70%, notably comprised between 5 and 60%. The transmittance is preferably measured on a SHIMADZU UV-1700 pharma Spec UV-Visible spectrophotometer at 25° C. with a wavelength of 600 nm.

Carboxylic acids (1) of the invention preferably provide a substituted or non-substituted alkyl chain comprising from 8 to 22 carbon atoms.

Preferred carboxylic acids (1) are chosen in the group consisting of: myristic acid, caprylic acid, capric acid, lauric acid, palmitic acid, stearic acid, oleic acid, linoleic acid, arachidic acid, behenic acid, erucic acid, ricinoleic acid, elaidic acid, arachidonic acid, myristoleic acid, and mixtures thereof.

One or several carboxylic acids (1) of the invention may be used in the gel system.

Amine (2) may be then an alkoxylated alkyl amine or an alkoxylated alkenyl amine. Amine (2) is defined as a compound providing an amine function and one or more alkoxylated chain and one or more alkyl chain or alkenyl chain. Preferentially the amine function is a secondary or tertiary amine function.

Preferably the alkoxylated alkyl amine or alkoxylated alkenyl amine compounds also comprise at least one hydroxyl function.

Alkoxylated alkyl amine compound preferably comprises a linear or branched, alkyl chain comprising from 8 to 22 carbon atoms. Alkoxylated alkenyl amine compound preferably comprises a linear or branched, alkenyl chain comprising from 8 to 22 carbon atoms.

Preferably, the alkoxylated alkyl amine compound comprises at least one hydroxyl function and at least one alkyl chain comprising from 8 to 22 carbon atoms. The alkoxylated alkenyl amine compounds preferably comprise at least one hydroxyl function and at least one alkenyl chain comprising from 8 to 22 carbon atoms.

According to one embodiment of the present invention, alkoxylated alkyl or alkenyl amine (2) is a compound of formula (I):

R—N—[(X—O)$_y$—H]$_2$    (I)

wherein:
R is selected from an alkyl or alkenyl group comprising from 8 to 22 carbon atoms
X is an alkyl chain containing 1 to 4 carbon atoms; and
y is 1, 2, 3, 4 or 5.

In the compounds of formula (I), R is preferably an alkyl or alkenyl group comprising from 12 to 22 carbon atoms, preferably a $C_{12}$-alkyl, $C_{12}$-alkenyl, $C_{14}$-alkyl, $C_{14}$-alkenyl, $C_{16}$-alkyl, $C_{16}$-alkenyl, $C_{18}$-alkyl, $C_{18}$-alkenyl, $C_{20}$-alkyl, $C_{20}$-alkenyl, $C_{22}$-alkyl and $C_{22}$-alkenyl. The number of carbons may be expressed as an average as alkoxylated alkyl or alkenyl amines may be derived from natural oils comprising a mixture of alkyl groups or alkenyl groups of somewhat varying length. Alkyl or alkenyl chains may be derived from tallow, coconut oil, soybean oil, palm oil, palm kernel oil and mixtures thereof.

X is preferably ethyl. y is preferably 2.

Preferred alkoxylated alkyl or alkenyl amines of the present invention are chosen in the group consisting of: bis(2-hydroxyethyl) hydrogenated tallow amine, bis(2-hydroxyethyl) lauryl amine, bis(2-hydroxyethyl) coco amine, bis(2-hydroxyethyl) myristyl amine, bis(2-hydroxyethyl) palmitoyl amine, bis(2-hydroxyethyl) stearyl amine, bis(2-hydroxyethyl) palm amine, bis(2-hydroxyethyl) palm kernel amine, bis(2-hydroxyethyl) tallow amine, bis(2-hydroxyethyl) oleyl amine, and mixtures thereof.

One or several alkoxylated alkyl or alkenyl amines may be used in the gel system of the invention.

The weight ratio of carboxylic acid (1)/amine (2) in the gel system is preferably comprised between 10:1 and 1:3, more preferably comprised between 3:1 and 1:3, more preferably comprised between 2:1 and 1:2. The weight ratio of carboxylic acid (1)/amine (2) in the gel system may also be comprised between 10:1 and 1:1, more preferably comprised between 6:1 and 2:1.

Cationic surfactants (3) of the formulation may be used singly or in admixture.

Cationic surfactant of the present invention is preferably a quaternary ammonium material. Examples of right cationic surfactants of quaternary ammonium types may be for example: ester quaternary ammonium, alkyl quaternary ammonium, amido quaternary ammonium, imidazoline quaternary ammonium, and ester amido quaternary ammonium.

Particularly preferred quaternary ammonium cationic surfactants comprises at least one alkyl or alkenyl chain, having from 8 to 22 carbon atoms, connected to the nitrogen head group, possibly with at least one ester function and/or amine function.

Suitable cationic surfactants for use in hair conditioners of the invention include quaternary ammonium compounds such as cetyl trimethyl ammonium bromide (also known as CETAB or cetrimonium bromide), cetyltrimethylammonium chloride (also known as cetrimonium chloride), myristyl trimethyl ammonium bromide (also known as myrtrimonium bromide or Quaternium-13), cetyl trimethyl ammonium chloride, stearyl dimethyl distearyldimonium chloride, dicetyl dimonium chloride, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, dicetyl dimonium chloride and distearyldimonium chloride; isostearylaminopropalkonium chloride or olealkonium chloride; behentrimonium chloride; coconut bis(2-hydroxyethyl) methyl ammonium chloride; stearyl bis(2-hydroxyethyl) methyl ammonium chloride; laurylamido propyl trimethul ammonium methylsulfate; behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof.

The weight ratio of carboxylic acid (1)/cationic surfactant (3) in the gel system is preferably comprised between 4:1 and 1:4, more preferably comprised between 3:1 and 1:2, more preferably comprised between 1.5:1 and 1:1.5.

The weight ratio of amine (2)/cationic surfactant (3) in the gel system may be comprised between 5:1 and 1:5. The weight ratio of amine (2)/cationic surfactant (3) in the gel system may also be comprised between 4:1 and 1:10, more preferably comprised between 4:1 and 1:4, more preferably comprised between 4:1 and 1:2, notably comprised between 2:1 and 1:6.

Gel system of the present invention may also comprise an amidoamine. Amidoamine may be defined as a compound providing an amine function and an amide function. Preferentially the amine function is a primary amine function.

Preferably the amidoamine is corresponding to the general formula (II):

$$R^1—CONH—(CH_2)_m N(R^2)(R^3) \quad (II)$$

wherein
- $R^1$ is a hydrocarbyl chain having 10 or more carbon atoms, preferably from about 11 to about 24 carbon atoms,
- $R^2$ and $R^3$ are, independently from each other, selected from hydrogen or a hydrocarbyl chains having from 1 to 10 carbon atoms, and
- m is an integer from 1 to about 10.

As used herein, the term hydrocarbyl chain means an alkyl or alkenyl chain. Preferred amidoamine compounds are those corresponding to formula (I) in which $R^2$ and $R^3$ are, independently from each other, hydrogen or alkyl group, having from 1 to about 4 carbon atoms, and m is an integer from 1 to about 4. Preferably, $R^2$ and $R^3$ are methyl or ethyl groups. Preferably, m is 2 or 3, i.e. an ethylene or propylene group.

Preferred amidoamines useful herein include stearamidopropyl dimethylamine, stearamidopropyl diethylamine, stearamidoethyl diethylamine, stearamidoethyl dimethylamine, palmitamidopropyl dimethylamine, palmitamidopropyl diethylamine, palmitamidoethyl diethylamine, palmitamidoethyl dimethylamine, behenamidopropyl dimethylamine, behenamidopropyl diethylamine, behenamidoethyl diethylamine, behenamidoethyl dimethylamine, arachidamidopropyl dimethylamine, arachidamidopropyl diethylamine, arachid-amidoethyl diethylamine, arachidamidoethyl dimethylamine, cetearyl-amidopropyl dimethylamine, cetearyl-amidopropyl diethylamine, lauryl-amidopropyl dimethylamine, lauryl-amidopropyl dimethylamine, coconut-amidopropyl dimethylamine, tallow-amidopropyl dimehtylamine, and mixtures thereof.

One or several amidoamines may be used in the gel system of the invention.

The weight ratio of carboxylic acid (1)/amidoamine in the gel system is preferably comprised between 5:1 and 1:5, more preferably comprised between 3:1 and 1:3, more preferably comprised between 1.5:1 and 1:1.5.

Gel system of the present invention preferably comprises at least:
(1) 1-10% by weight of a carboxylic acid having an alkyl or alkenyl chain comprising from 8 to 22 carbon atoms;
(2) 1-10% by weight of an alkoxylated alkyl or alkenyl amine;
(3) 0.5-5% by weight of a cationic surfactant;
(4) water and
1-10% by weight of an amidoamine.

The invention also concerns a gel system susceptible to be obtained by mixing at least:
(1) 1-10% by weight of a carboxylic acid having an alkyl or alkenyl chain comprising from 8 to 22 carbon atoms;
(2) 1-10% by weight of an alkoxylated alkyl or alkenyl amine;
(3) 0.5-5% by weight of a cationic surfactant;
(4) water and
1-10% by weight of an amidoamine.

The compositions of the present invention may also comprise other components such as surfactants, organic or inorganic thickeners such as hydroxyethyl cellulose, opacifying or pearlescent agents such as for example ethyleneglycol distearate, water-insoluble skin benefit agents, exfoliating particles, preservatives, antimicrobials, bactericides, antioxydants such as butylated hydroxytoluene, humectants, fragrances, colouring agents and sequestering agents such as for example sodium salt of the ethylenediaminetetraacetic acid.

The humectants in the composition may be selected from glycerine, diols, triols and polyols. The composition may comprise from 0 to 10% by weight of humectants, based on the total weight of the composition.

The surfactants in the composition may be selected from any known anionic, cationic, nonionic and amphoteric/zwitterionic surfactants suitable for applications to the human body.

Preferably, the gel system of the invention is substantially free or, in some cases, completely free of silicone, such as dimethicone. As used herein, the term "substantially free" when used with reference to the absence of silicone in the gel system of the present invention, means that the gel system comprises less than 0.1% wt of silicone, based on the total weight of the gel system. As used herein, the term "completely free" when used with reference to the absence of silicone in the gel system of the present invention, means that the gel system comprises no silicone at all.

The gel system according to the present invention can be easily produced for example by melting and mixing at least components (1), (2) and (3), notably simultaneously or separately, notably by heating and thereafter cooling the mixture, for example at room temperature, such as 25° C.

The present invention also concerns a process to produce the gel system wherein at least the carboxylic acid (1), the amine (2) and the cationic surfactant (3) are mixed together, notably simultaneously or separately, under heating.

The gel system according to the present invention may notably be obtained by heating the carboxylic acid (1) and the amine (2) until they are molten, separately heating a cationic surfactant (3) in water until it is dissolved/suspended, then adding the molten carboxylic acid (1) and the amine (2) mix to the cationic surfactant (3), notably before adding any remaining ingredients.

The gel system according to the present invention may also be obtained by heating the carboxylic acid (1) and the amine (2) and the cationic surfactant (3) until they are molten, separately heating a water phase until it is dissolved/suspended, then adding the molten mixture to the water phase, notably before adding any remaining ingredients.

The gel system according to the present invention may also be obtained by heating the carboxylic acid (1) and the amine (2) and amidoamine and the cationic surfactant (3) until they are molten, separately heating a water phase, then adding the molten mixture to the water phase, notably before adding any remaining ingredients.

The examples provided here further describe and demonstrate embodiments of the present invention. The examples are given solely for the purpose of illustration and are not to be construed as limitation of the present invention

EXPERIMENTAL PART

Compounds used in the formulations are the following:
Ethyl fatty amine is hydrogenated tallow amine ethoxylate ether (2EO). Fentacare HT02 from Rhodia
Bis(2-hydroxyethyl) tallowalkyl amine (2EO), Fentacare T02 from Solvay
Cationic surfactant is behenyl trimethylammonium chloride (BTAC). BTAC 2231 from Rhodia
Cetearylamidopropyl dimethylamine, Fentamine PKO 1865 from Solvay

Example 1: Formulations

1. In a side beaker, heat the D.I. water up to 80° C.
2. In the main beaker, add myristic acid, Fentacare HT02 and BTAC 2231, use IKA mechanical overhead stirrer to stir at 50 rpm while heating up to 80° C. When the mixture is melt and becomes clear, pour the pre-heated D.I. water in Step 1 into the main beaker, maintain the temperature of 80° C., stir at 1000 rpm for 2 minutes.
3. Remove heat, stir at 400 rpm to cool down the system.
4. When temperature is below 45° C., add Mackstat DM, stir for another 15 minutes, stop stirring and cool down to room temperature.
5. Discharge.

Apparent Viscosity Measurement

The apparent viscosity is measured on a Brookfield DV-II+ viscometer at 25° C., 10 rpm for 1 minute Transmittance Measurement Transmittance is measured on a SHIMADZU UV-1700 pharma Spec UV-Visible spectrophotometer at 25° C. with a wavelength of 600 nm.

Conditioning Effect Measurement (Dia-Stron Wet/Dry Combing)

The changes in the wet and/or dry combing attributes of hair resulting from treatment with shampoos, conditioners, styling aids or other active materials were measure using DIA-STRON MTT-170 (Miniature Tensile Tester) as follows.

Materials and Equipment:
Dia-Stron MTT 170
Dia-Stron software "UVWin 1.29.4000"
IBM compatible computer and printer
Hair tresses (2 grams, 6 inches long, net 1 inch wide, soft swatch—International Hair Importers, N.Y.)
Coarse comb (4-tine/cm) for combing hair
Fine comb (6-tine/cm) to be attached on Dia-Stron fixed arm
Standard rinsing apparatus: tray filled with running water (temp ~25-40° C.; flow-rate ~1.8 L/min)

Experimental conditions: with the exception of pre-treatment and treatment of hair tresses, all procedures should be conducted in a humidity and temperature-controlled room (60% relative humidity, 21-22° C.)

Procedures to be carried out:
1. Pre-treatment of hair tresses/To remove residual conditioning agents and other impurities
2. Wet combing (sorting)/For sorting of hair tresses
3. Dry combing (untreated)/Base line of dry, untreated tresses
4. Wet combing (untreated)/Base line of wet, untreated tresses
5. Treatment of hair tresses with test shampoo, conditioners, styling aids or other active materials formulations
6. Dry combing (treated)/Effect of treatment and conditioning
7. Wet combing (treated)/Effect of treatment and conditioning

*Note:
1 hair tress=10 combings
1 test sample=3 hair tresses
3 hair tresses×10 combings=30 combings per test sample Data Processing:

Conditioning Effect(Total Work Reduction)=(Treated Dry−Untreated Dry)/Untreated Dry %

Conditioning Effect(Total Work Reduction)=(Treated Wet−Untreated Wet)/Untreated Wet %

Conditioning Effect(Greatest Force)=(Treated Dry−Untreated Dry)/Untreated Dry %

Conditioning Effect(Greatest Force)=(Treated Wet−Untreated Wet)/Untreated Wet %

Results expressed in Tables 1 and 2 as follow demonstrate that formulations Inv. 1-5 according to the invention provide the desired appearance and conditioning effect while the other formulations are either lack of desired conditioning effect or sufficient viscosity and transmittance.

TABLE 1

|  | Inv 1 | Inv 2 | Inv 3 | Inv 4 | Inv 5 |
|---|---|---|---|---|---|
| Formulations |  |  |  |  |  |
| (1) Acid (% by wt) | Myristic Acid (3.5) | Myristic Acid (2.8) | Myristic Acid (3.5) | Myristic Acid (3.5) | Myristic Acid (3.5) |
| (2) Amine (% by wt) | Hydroxyl ethyl fatty amine (5.0) | Hydroxyl ethyl fatty amine (4.0) | Hydroxyl ethyl fatty amine (2.0) | Hydroxyl ethyl fatty amine (3.5) | Hydroxyl ethyl fatty amine (5) |
| (3) Cationic surfactant (% by wt) | 2.5 | 2.4 | 2.5 | 3.75 | 1.25 |
| (4) Glycerine (% by wt) | — | 3.0 | — | — | — |
| (5) Water | To 100 | To 100 | To 100 | To 100 | To 100 |
| Properties |  |  |  |  |  |
| Gel obtaining | Yes and stable | Yes and stable | Yes and stable | Yes and stable | Yes and stable |

TABLE 1-continued

|  | Inv 1 | Inv 2 | Inv 3 | Inv 4 | Inv 5 |
|---|---|---|---|---|---|
| Viscosity (cps) | 40400 | 14200 | 12000 | 3900 | 22200 |
| Transmittance (%) | 8.5 | 5 | 7.0 | 13.0 | 12.0 |
| Conditioning effect (%) | +46 | +76 | +83 | +90 | +92 |

TABLE 2

|  | Comp 1 | Comp 2 | Comp 3 |
|---|---|---|---|
| Formulations |  |  |  |
| (1) Acid (% by wt) | — | Myristic Acid (3.5) | Citric Acid (3.5) |
| (2) Amine (% by wt) | Hydroxyl ethyl fatty amine (5.0) | Stearyl Amine (5.0) | Hydroxyl ethyl fatty amine (5.0) |
| (3) Cationic surfactant (% by wt) | 2.5 | 2.5 | 2.5 |
| (4) Water | To 100 | To 100 | To 100 |
| Properties |  |  |  |
| Gel obtaining | Yes and stable | Yes and Stable | No gel achievement, unstable and phase separation |
| Viscosity (cps) | 25400 | 39600 | 100 |
| Transmittance (%) | 5 | 0 | 85 |
| Conditioning effect (%) | −157 | +54 | +87 |

It appears then that the gel system of the present invention provides an excellent conditioning effect, notably for washing skin and/or hair, and a high transmittance.

Example 2: Storage Stability of Formulations

Formulations are produced as expressed in the previous examples and according to Table 3 as follows.

Temperature stability is measured as follows: formulation samples were put into 25° C., 45° C. oven and 4° C. freezer respectively. Appearance is visually checked every week. Results are expressed in Table 3.

TABLE 3

|  | C1 | C2 | C3 | Inv 1 |
|---|---|---|---|---|
| Formulations |  |  |  |  |
| Acid or alcohol (% by wt) | Myristic Acid (3.5) | Stearyl alcohol (20) | Myristic Acid (3.5) | Myristic Acid (3.5) |
| Amidoamine (% by wt) | Cetearyl amidopropyl dimethylamine (4.0) | Cetearyl amidopropyl dimethylamine (2.0) | — | Cetearyl amidopropyl dimethylamine (3.0) |
| Alkoxylated Amine (% by wt) | — | — | — | Bis (2-hydroxyethyl)tallowalkyl amine (1.0) |
| Cationic surfactant (% by wt) | 3.0 | 10.0 | 2.5 | 3.0 |
| Other (% by wt) | — | — | Stearyl amine (5.0) | — |
| Water | To 100 | To 100 | To 100 | To 100 |
| Properties |  |  |  |  |
| Gel obtaining | Translucent Gel | Opaque white cream | Opaque white cream | Translucent Gel |
| Viscosity (cps) | 45000 | >100000 | 39600 | 16000 |
| Transmittance (%) | 11 | 0 | 0 | 10 |
| Conditioning effect (%) | +75 | +81 | +54 | +73 |
| Appearance at 4° C., 4 weeks | Very turbid | Opaque and white | Opaque and white | Translucent |
| Appearance at 25° C., 4 weeks | Translucent | Opaque and white | Opaque and white | Translucent |
| Appearance at 45° C., 4 weeks | Translucent | Opaque and white | Opaque and white | Translucent |

It appears then that the gel system of the present invention provides an excellent conditioning effect, a high transmittance and a very good time and temperature stability notably in comparison with comparative formulations that provide a very low transmittance, below 1% after a storage at low temperature.

The invention claimed is:

1. A gel system, comprising:
   (1) from 1 to 10% by weight of a carboxylic acid having an alkyl or alkenyl chain comprising from 8 to 22 carbon atoms;
   (2) from 1 to 10% by weight of an alkoxylated alkyl or alkenyl amine;
   (3) from 0.5 to 5% by weight of a cationic surfactant; and
   (4) water.

2. The gel system according to claim 1, wherein said gel exhibits an apparent viscosity between 1000 and 100000 cps.

3. The gel system according to claim 1, wherein carboxylic acids are chosen from the group consisting of myristic acid, caprylic acid, capric acid, lauric acid, palmitic acid, stearic acid, oleic acid, linoleic acid, arachidic acid, behenic acid, erucic acid, ricinoleic acid, elaidic acid, arachidonic acid, myristoleic acid, and mixtures thereof.

4. The gel system according to claim 1, wherein the alkoxylated alkyl or alkenyl amine compound also comprises at least one hydroxyl function.

5. The gel system according to claim 1, wherein alkoxylated alkyl or alkenyl amine compound is a compound according to formula (I):

R—N—[(X—O)$_y$—H]$_2$                (I)

wherein:
   R is selected from alkyl and alkenyl groups, each comprising from 8 to 22 carbon atoms per group;
   X is an alkyl group containing 1 to 4 carbon atoms; and
   y is 1, 2, 3, 4 or 5.

6. The gel system according to claim 5, wherein R is an alkyl or alkenyl group that comprises from 12 to 22 carbon atoms per group.

7. The gel system according to claim 5, wherein X is ethyl.

8. The gel system according to claim 1, wherein y is 2.

9. The gel system according to claim 1, wherein alkoxylated alkyl or alkenyl amines are chosen from the group consisting of bis(2-hydroxyethyl) hydrogenated tallow amine, bis(2-hydroxyethyl) lauryl amine, bis(2-hydroxyethyl) coco amine, bis(2-hydroxyethyl) myristyl amine, bis (2-hydroxyethyl) palmitoyl amine, bis(2-hydroxyethyl) stearyl amine, bis(2-hydroxyethyl) palm amine, bis(2-hydroxyethyl) palm kernel amine, bis(2-hydroxyethyl) tallow amine, bis(2-hydroxyethyl) oleyl amine, and mixtures thereof.

10. The gel system according to claim 1, wherein the weight ratio of carboxylic acid/amine in the gel system is between 3:1 and 1:3.

11. The gel system according to claim 1, wherein the cationic surfactant is a quaternary ammonium material.

12. The gel system according to claim 1, wherein the weight ratio of carboxylic acid/cationic surfactant in the gel system is between 4:1 and 1:4.

13. The gel system according to claim 1, wherein the weight ratio of amine/cationic surfactant in the gel system is comprised 5:1 and 1:5.

14. The gel system according to claim 1, wherein it comprises a humectant.

15. The gel system according to claim 1, wherein said gel system is substantially free or completely free of silicone.

16. The gel system according to claim 1, wherein said gel system comprises an amidoamine.

17. The gel system according to claim 1, wherein said gel system comprises an amidoamine according to the general formula (II):

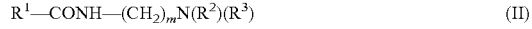

R$^1$—CONH—(CH$_2$)$_m$N(R$^2$)(R$^3$)                (II)

wherein
   R$^1$ is a hydrocarbyl chain comprising 10 or more carbon atoms,
   R$^2$ and R$^3$ are, independently from each other, selected from the group consisting of hydrogen and hydrocarbyl chains comprising from 1 to 10 carbon atoms per chain, and
   m is an integer from 1 to about 10.

18. A process to produce a gel system according to claim 1, wherein at least the carboxylic acid, the amine and the cationic surfactant are mixed together under heating.

19. The process according to claim 18, wherein the gel system is obtained by:
   heating the carboxylic acid and the amine until they are molten,
   separately heating a cationic surfactant in water until it is dissolved or suspended, then
   adding the molten carboxylic acid and the amine mix to the cationic surfactant.

20. A gel system made by mixing at least the following components:
   (1) from 1 to 10% by weight of a carboxylic acid having an alkyl or alkenyl chain comprising from 8 to 22 carbon atoms;
   (2) from 1 to 10% by weight of an alkoxylated alkyl or alkenyl amine;
   (3) from 0.5 to 5% by weight of a cationic surfactant; and
   (4) water.

21. The gel system of claim 1, wherein the gel system is a hair conditioning gel.

* * * * *